US005565199A

United States Patent [19]
Page et al.

[11] Patent Number: 5,565,199
[45] Date of Patent: Oct. 15, 1996

[54] SYSTEMS AND METHODS FOR THE SYNTHESIS OF NATURAL BASE STEROIDAL HORMONES AND MORE ESPECIALLY ESTROGENS AND PROGESTERONE AND ESTROGEN-LIKE AND PROGESTERONE-LIKE COMPOUNDS AND THEIR DERIVATIVES DERIVED AS PHYTOHORMONES FROM HERBACEOUS PLANTS

[76] Inventors: Elliot W. Page; Linda G. Rector-Page, both of 300 Country Club Heights, Carmel Valley, Calif. 93924

[21] Appl. No.: 384,914

[22] Filed: Feb. 7, 1995

[51] Int. Cl.$^6$ .................................................. A61K 75/78
[52] U.S. Cl. ........................ 424/195.1; 514/182; 514/874
[58] Field of Search .................................... 514/182, 874; 424/195.1

[56] References Cited

U.S. PATENT DOCUMENTS

| | | | |
|---|---|---|---|
| 2,096,744 | 10/1937 | Hildebrandt | 260/153 |
| 2,361,847 | 10/1944 | Inhoffen | 260/397.5 |
| 2,611,773 | 9/1952 | Ott | 260/397.5 |
| 4,863,898 | 9/1989 | Ashmead et al. | 514/6 |

OTHER PUBLICATIONS

Tyler et al, Pharmacognosy, 1988, pp. 4, 17–19, 22, 62–64, 67–70, 460, 462, 464, 469, 473–475, 486.
BA 76:90410, Xu et al, J. Tradit Chin Med 2(3) 1982, 179–181.
BA 84:101752, Usuki, Jpn J Fertil Steril, 32(1), 1987, 1–4.
CA 75:8522, Tuskaev, Rast. Resur, 7(2), 1971, 295–8.
Remington's Pharmaceutical Sciences, 15th ed., 1975, pp. 273–274, 322–339, 1442–1452, 1536–1537.
"Nature's Pharmacy: Top Five Herbs for Women," *Delicious!*, May/Jun. 1993, p. 56.
Daniel B. Mowrey, "Herbs to Relieve Menstrual Disorders," *Let's Live*, Dec. 1990, pp. 66–68.
William Lee, *Herbs and Herbal Medicine—Their Variety of Uses as Foods and Medicine*, Keats Publishing, Inc. New Cannan, Connecticut, pp. 14–15.
Jill Neimark, "Natural Hormones," *To Your Health*, Jan./Feb., p. 1.
Helen Pensanti, "Natural Hormones Made Easy," P.O. Box 11959, Santa Ana, California.
Rudolf Fritz Weiss, "Herbal Medicine," 1988, p. 330.
"Change–O–Life® Formula," *Herbel Formulas*, p. 30, published advertisement of Nature's Way Products, 10 Mountain Springs Parkway, Springville, Utah.
Russell E. Marker, D. L. Turner and Paul R. Ulshafer, "Sterols. CIV. Diosgenin from Certain American Plants," vol. 62, Sep. 1940, pp. 2542–2543.
*Natural Healing With Herbs*, pp. 110–111.
"Natural Relief for Menopause," *Let's Live*, Nov. 1992, p. 48.
"Pro–Gest®," published advertisement of Professional & Technical Services, Inc., 3331 N.E. Sandy Blvd., Portland, Oregon.

Lita Lee, "Notes on Estrogen and Progesterone," from *Nutrition for Women* by Raymond F. Peat.
"Suggested Application of Pro–Gest and Es–Gen Body Creams for Menopausal and Postmenopausal Women," published advertisement of Professional Technical Service, Inc., 3331 N.E. Sandy Blvd., Portland, Oregon.
George Nobbe, "Reversing Osteoporosis," *Longevity*, Mar., 1991.
Leslie Laurence, "Beyond Estrogen Replacement Therapy," Health and Fitness, *San Jose Mercury News*, Jul. 6, 1994.
Michael T. Murray, "The Healing Properties of Licorice," *Health Counselor*, Nov./Dec. 1991, pp. 17–19.
Colleen Kent, "Licorice—More than Just Candy," *ATOMS (Autralian Traditional Medicine Society Ltd.)*, Autumn 1994, pp. 9–14.
Terry Willard, "Licorice," *The Wild Rose Scientific Herbal*, 1991, pp. 206–210.
Michael Murray, Information sheet for "Angelica Sinesis (Dong Quai): An Herbal Formula for Symtoms of Menstrual Discomfort." Rosalba Belford/Courtney, "Comparison of Chinese and Western Uses of Angelica Sinensis," *Australian Journal of Medical Herbalism*, vol. 5, Issue 4, Dec. 1993, pp. 87–91.
"Born Again™ Wild Yam Cream with Vitamin E," published advertisement of Alvin Last, Inc., Yonkers, New York.
"Wild Yam: *Dioscorea villosa*, L.," pp. 301–302.
"Female Tonic," *The Scientific Validation of Herbal Medicine*, pp. 111–112.
David Steinman, "Treating PMS Without Side Effects," published advertisement of L&H Vitamins Inc.
Paul Bergner, "Wild Yam and Hormonal Synthesis,"*Medical Herbalism*, vol. 4, No. 4, Winter 1992.
James A. Duke, *CRC Handbook of Medical Herbs*, 1985, p. 168.
"Botanical extracts: Natural Hormone Precursors," *Health Counselor*, vol. 4, No. 1, p. 35.
"Kathi Keville: A Natural Woman," *Delicious!*, Jul./Aug. 1990, p. 18.
Steve Blake, GlobalHerb Date Base, Felton, 1994.

Primary Examiner—John W. Rollins
Attorney, Agent, or Firm—Berne S. Broadbent; Gary D. E. Pierce; A. John Pate

[57] ABSTRACT

Systems and methods for synthesizing natural base steroidal hormones and more especially estrogens and progesterone and estrogen-like and progesterone-like compounds and their derivatives which are derived in the form of phytohormones from herbaceous plants and formulated to provide a broad spectrum of estrogenic and/or progesterone activity for influencing physiological processes and biological functions. In particular, phytohormones (i.e. phytoestrogens and/or phytoprogesterone) are synthesized from herbaceous compounds selected from a group consisting of plants having a propensity for simulating estrogenic and/or progesterone hormonal activity that, when entering the bloodstream of a biological organism, either by means of oral ingestion, parenteral injection, or topical application, have a tendency to enhance, supplement and/or maintain estrogen and/or progesterone hormonal levels by means of replacement therapy within a biological organism.

19 Claims, No Drawings

SYSTEMS AND METHODS FOR THE SYNTHESIS OF NATURAL BASE STEROIDAL HORMONES AND MORE ESPECIALLY ESTROGENS AND PROGESTERONE AND ESTROGEN-LIKE AND PROGESTERONE-LIKE COMPOUNDS AND THEIR DERIVATIVES DERIVED AS PHYTOHORMONES FROM HERBACEOUS PLANTS

BACKGROUND

1. The Field of the Invention

This invention relates to steroidal hormones and, more particularly, to novel systems and methods for synthesizing natural base steroidal hormones and more especially estrogens and progesterone and estrogen-like and progesterone-like compounds and their derivatives derived as phytohormones from herbaceous plants.

2. The Background Art

Hormones are glandular chemical secretions generally formed by an organ or part of the body and carried in the bloodstream to another organ or part of the body to stimulate or retard a specific physiological activity or process. Steroidal hormones are a distinctive type of hormone which encompasses a large group of chemical compounds that are widely distributed throughout the body and involved in many important structural and functional physiological roles.

A principle component of steroidal hormones is its molecular configuration which incorporates a cyclopentanoperhydrophenanthrene ring system, commonly referred to as the "steroid nucleus." The steroid nucleus is generally characterized as consisting of three fused cyclohexane rings and a terminal cyclopentane ring of carbon atoms formed in a nonlinear or phenanthrene arrangement which provides the structural basis for many important compounds such as estrogens, progesterone, and androgens.

Estrogens include any of various natural or synthetic substances possessing the biological activity of estrus-producing hormones. Typically formed in the ovary, placenta, testis, adrenal cortex and by some plants, estrogens are generally responsible for stimulating the development and maintenance of the female secondary sex characteristics.

In general structure, estrogen consists of a group of three estrogenic hormones—estradiol ($C_{18}H_{24}O_2$), estrone ($C_{18}H_{22}O_2$), and estriol ($C_{18}H_{24}O_3$)—which are synthesized mainly in the liver from cholesterol and typically transported in the circulatory system both in free and conjugated forms (approximately 50% or more are bound to plasma proteins). In function, estrogens enter target cells and bind to receptors where they influence protein synthesis and promote enzyme activation. Because estrogen is weakly anabolic, its primary anabolic targets are the secondary sex organs. However, estrogens also promote protein synthesis in other body tissues, and some tissue wasting (particularly of skeletal tissue) occurs in the absence of estrogen, as demonstrated by the rapid acceleration of osteoporosis in postmenopausal women.

Under the influence of estrogenic hormones, estrogen has been found to decrease platelet adhesiveness, increase serum levels of vitamin K-dependent clotting factors, depress the release of gonadotropins (follicle-stimulating hormone and luteinizing hormone) secreted by the anterior pituitary which influence female reproductive cycles, and suppress lactation in postpartum women. Other significant metabolic effects of estrogenic hormones include, for example: (1) depression of bone resorption, conservation of calcium and phosphorus, epiphyseal closure and enhancement of bone formation; (2) modification of carbohydrate absorption and metabolism by reducing intestinal motility (and thus the rate of sugar absorption) and by antagonizing the hypoglycemic activity of insulin; (3) alteration of liver metabolism, which results in higher plasma levels of thyroxin and cortisol binding proteins; and (4) enhancement of ($\alpha$)-lipoprotein and triglyceride plasma levels and depression of ($\beta$)-lipoprotein and cholesterol plasma levels.

Progesterone is another important steroidal hormone which is generally responsible for facilitating a significant physiological role in the luteal phase of the menstrual cycle and in the maintenance of a pregnancy. Formed in the corpus luteum, adrenals, testes, and placenta during pregnancy, progesterone ($C_{21}H_{30}O_2$) typically regulates the periodicity of the sexual cycle, facilitates changes in the endometrium, adapting it for the reception of the fertilized ovum, stimulates the mammary glands, inhibits uterine musculature, and relaxes the pelvic ligaments.

Like estrogen, progesterone enters target cells and binds to receptors to influence protein synthesis. One of the predominant physiologic effects of progesterone in nonpregnant women is to promote changes in the estrogen-primed endometrium in order to convert the endometrium into a secretory mucosa. Progesterone further inhibits spontaneous uterine contractions, and at high doses can restrict the release of hypothalamic gonadotropin-releasing hormones. Moreover, high doses of progesterone generally suppress endometrial bleeding, whereas the withdrawal of progesterone typically induces endometrial sloughing and has been found to have antineoplastic activity against some cancers. While both estrogen and progesterone are necessary to produce the normal endometrial cycle, progesterone's metabolic effects are generally fewer than those of estrogen.

Based on the foregoing, physiologists agree that steroidal hormones play a major role in producing the cyclic changes characteristic in women, in addition to facilitating several other important physiological activities and processes in the body. Consequently, a hormone imbalance of estrogen and/or progesterone can have serious physiological consequences.

Therapeutic uses of steroidal hormone replacement therapy (with natural or synthetic preparations) have been developed by those skilled in the art and are being used clinically as means for increasing or supplementing the hormone balance of biological organisms, as well as for treating a wide variety of other clinical conditions. For example, the normal female reproductive system generally depends on the proper sequential balance of ovarian hormones and is, thereby, acutely susceptible to hormonal interference or imbalance. In this regard, ovarian hormones (or their synthetic analogs) have been used as a form of hormonal replacement therapy to treat various types of gynecologic and physiologic problems.

For example, as a woman ages, the functional life of the ovaries generally declines. During menopause, estrogen secretion typically declines slowly and continues for several years after menses has ended. This decline in estrogen may cause symptoms such as hot flashes and inappropriate sweating (vasomotor symptoms), palpitations, and atrophic vaginitis. Headaches, dizziness, fainting, paresthesia, and muscle and joint aches, as well as feelings of anxiety or emotional lability, may also occur. More importantly, osteoporosis commonly develops in post menopause women and is generally associated with estrogen deficiency.

The National Institute of Health Consensus Development Conference on Osteoporosis concluded that estrogen replacement therapy is one of the most effective single modalities in the prevention of osteoporosis. Consistent therewith, estrogen replacement therapy has been found to be arguably more effective at preventing osteoporosis than reversing it, and should be typically started early after menopause.

Important indications for estrogen-only hormone preparations typically relate to three major use categories: (1) replacement therapy in girls with primary hypogonadism, and relief of vasomotor symptoms in menopausal women; (2) to moderate the intensity of treatment of advanced breast or prostate cancer; and (3) treatment of estrogen deficiency relative to induced osteoporosis. Similarly, important indications for progesterone-only hormonal preparations typically relate to: (1) the treatment of functional uterine bleeding and some types of amenorrhea; (2) adjunctive and palliative therapy for metastatic endometrial or renal carcinoma and endometriosis; and (3) the investigational use of progesterone replacement therapy as a long-acting contraceptive in females.

Estrogens are commonly used in combination with progesterone to provide a broad application of use as oral contraceptive agents. Similarly, progesterone may be used to supplement estrogen replacement therapy to reduce the risk of endometrial hyperstimulation.

Preparations of estrogenic or progesterone hormones for clinical use are broadly classified into two categories: (1) natural estrogens or progesterone, their esters and semisynthetic derivatives; and (2) synthetic nonsteroidal compounds having estrogenic or progesterone activity.

Metabolically, endogenous estrogen is metabolized and conjugated to glucuronides or sulfates by the liver. Normally, a small amount of estrogen is secreted into the bile, reabsorbed by intestinal cells, and recirculated back to the liver. However, the bulk of estrogen metabolites are eliminated in the urine. In this regard, urine from pregnant mares is typically a major source of "natural" estrogen synthesized for commercial use. Moreover, since β-estradiol ($C_{18}H_{24}O_2$) is considered the most potent estrogen secreted by the ovary, estradiol or its metabolites are commonly used in drug preparations of non-synthetic estrogens.

Chemically processed synthetic estrogens being produced by those skilled in the art may include, for example, ethinyl estradiol ($C_{20}H_{24}O_2$) and mestranol ($C_{21}H_{26}O_2$) which are typically used therapeutically as oral contraceptives. Estrogenic hormones being used for the therapeutic treatment of cancer may include, for example, diethylstilbestrol ($C_{18}H_{20}O_2$) and ethinyl estradiol. Diethylstilbestrol and ethinyl estradiol, however, may cause nausea and occasional vomiting. Other side-effects may involve the retention of sodium which may lead to hypertension and congestive heart failure. Accordingly, the blood pressure and cardiac status should be monitored periodically, especially when renal or cardiac disease is present. Other potential side effects are feminization and gynecomastia in males, and vaginal bleeding and breast tenderness in females.

Synthetic progesterone, such as megestrol acetate ($C_{24}H_{32}O_4$) and medroxyprogesterone acetate ($C_{22}H_{32}O_3$), were developed by those skilled in the art and may be used in the therapeutic treatment of advanced endometrial cancer and other hormone-dependent cancers. Chemically processed megestrol acetate and medroxyprogesterone acetate may also be used in conjunction with traditional anticancer drugs, surgery, and/or radiation therapy. Since these synthetic drugs are metabolized in the liver, they should be used cautiously in patients with liver dysfunction. In addition, progesterone therapy may cause vaginal bleeding, mild fluid retention, and hypercalcemia in patients with bone metastases.

Despite the wide-spread and growing use of hormonal replacement therapy of the type described above, the advantages and effectiveness of such prior art processed chemical base steroidal hormones has been clinically questioned as a result of the multiplicity of their serious physiological side effects. For example, estrogen-induced side effects of estrogen replacement therapy include, for example: (1) breast tenderness, enlargement, or secretion; breakthrough bleeding, changes in menstrual flow, dysmenorrhea, or amenorrhea during and after treatment; (2) a syndrome resembling premenstrual syndrome; (3) vaginal candidiasis; (4) changes in cervical eversion and cervical secretions; (5) a cystitis-like syndrome; (6) endometrial cystic hyperplasia; and (7) uterine fibromyomata. Estrogen replacement therapy may also cause changes in the libido. Headaches (including migraines), dizziness, chorea, and seizures have also been reported along with elevated blood pressure which is typically a common factor during estrogen replacement therapy.

The usual complaints associated with progesterone replacement therapy include, for example, gastrointestinal upset, headaches, and dizziness. Prolonged administration of high doses of progesterone (either natural or synthetic preparations) typically enhances gastrointestinal disturbances and usually promotes edema, weight gain, breast congestion, and menstrual abnormalities. Other effects include, for example, thromboembolism, cholestatic jaundice, depression, breakthrough bleeding, amenorrhea, insomnia, alopecia, acne, and hirsutism.

In addition to the serious side effects of chemically processed steroidal hormones, other practical problems with the prior art chemical base steroidal hormones have also emerged. For example, the cost of producing natural or synthetic steroidal hormones, such as estrogens and progesterone, can raise the market price of the drug to the point that hormonal replacement therapy becomes an unaffordable solution.

As illustrated by the various processed chemical base natural or synthetic steroidal hormone preparations which have been produced by those skilled in the art, efforts are continuously being made in an attempt to remedy the numerous therapeutic disadvantages and physiological contraindications associated with prior art steroidal hormones being used for replacement therapy. Consistent therewith, none of the prior art disclosures suggest the present compositions or methods for producing natural base steroidal hormones such as estrogens and progesterone and estrogen-like and progesterone-like compounds and their derivatives derived as phytohormones from herbaceous plants, as herein described and claimed.

BRIEF SUMMARY AND OBJECTS OF THE INVENTION

In view of the foregoing, it is a primary object of the present invention to provide systems and methods for synthesizing natural base steroidal hormones such as estrogens and progesterone and estrogen-like and progesterone-like compounds and their derivatives derived as phytohormones (phytoestrogens and/or phytoprogesterone) from herbaceous plants and which are capable of providing means for balancing estrogen and progesterone hormone levels in biological organisms without encouraging undesirable physiological side effects and/or therapeutic contraindications.

It is also an object of the present invention to provide means of delivering natural base steroidal hormones such as estrogens and progesterone and estrogen-like and progesterone-like compounds and their derivatives derived as phytohormones (phytoestrogens and/or phytoprogesterone) from herbaceous plants to specific target sites within a living organism for enhancing, supplementing, and/or maintaining estrogenic and progesterone hormonal levels in order to assist hormone-dependent body functions and physiological processes within biological organisms.

Further, it is an object of the present invention to provide systems and methods for synthesizing natural base steroidal hormones such as estrogens and progesterone and estrogen-like and progesterone-like compounds and their derivatives derived as phytohormones (phytoestrogens and/or phytoprogesterone) from herbaceous plants and which are sufficiently stable when properly formulated, in that they are readily absorbed into biological systems and transported to target sites for utilization.

It is a still further object of the present invention to provide systems and methods for synthesizing natural base steroidal hormones such as estrogens and progesterone and estrogen-like and progesterone-like compounds and their derivatives derived as phytohormones (phytoestrogens and/or phytoprogesterone) from herbaceous plants and which are formulated having one or more hormonal compounds to increase its effectiveness on hormone balancing.

Similarly, it is an object of the present invention to provide systems and methods for synthesizing natural base steroidal hormones such as estrogens and progesterone and estrogen-like and progesterone-like compounds and their derivatives derived as phytohormones (phytoestrogens and/or phytoprogesterone) from herbaceous plants and which are formulated as a natural dietary food supplement, whereby a biological organism can discard what is not needed.

In addition, it is an object of the present invention to provide systems and methods for synthesizing natural base steroidal hormones such as estrogens and progesterone and estrogen-like and progesterone-like compounds and their derivatives derived as phytohormones (phytoestrogens and/or phytoprogesterone) from herbaceous plants and which are produced at a very minimal cost.

Consistent with the foregoing objects, and in accordance with the invention as embodied and broadly described herein, these and other objects may be accomplished by means of synthesizing natural base steroidal hormones and more especially estrogens and progesterone and estrogen-like and progesterone-like compounds and their derivatives derived as phytohormones (phytoestrogens and/or phytoprogesterone) from herbaceous plants and formulated to provide a broad spectrum of estrogenic and/or progesterone activity for influencing physiological processes and biological functions. In particular, phytohormones are synthesized from herbaceous compounds selected from a group consisting of plants having a propensity for simulating estrogenic and/or progesterone activity that, when entering the bloodstream of a biological organism, either by means of oral ingestion, parenteral injection, or topical application, have a propensity to enhance, supplement and/or maintain estrogen and/or progesterone hormonal levels within the biological organism.

DETAILED DESCRIPTION OF THE PREFERRED EMBODIMENTS

It will be readily understood that the composition of the present invention, as generally described and illustrated in the Examples herein, could be synthesized in a variety of formulations. Thus, the following more detailed description of the presently preferred embodiments of the methods, formulations, and compositions of the present invention, as represented in Examples I through XII, is not intended to limit the scope of the invention, as claimed, but it is merely representative of the presently preferred embodiments of the invention.

The systems and methods of the present invention for synthesizing natural base steroidal hormones and more especially estrogens and progesterone and estrogen-like and progesterone-like compounds and their derivatives derived as phytohormones from herbaceous plants provide a broad spectrum of estrogenic and/or progesterone hormone activity to enhance, supplement, and/or maintain hormonal levels in biological organisms and influence physiological processes and biological functions. The present invention comprises systems and methods for synthesizing and formulating natural base steroidal hormones from phytoestrogens and phytoprogesterone, as compared to prior art chemically processed steroidal hormones typically having harmful physiological side effects and therapeutic contraindications.

Typically, herbaceous plants contain many chemically and physiologically distinct types of plant-regulating substances, some of which are properly called phytohormones. In this regard, the systems and methods for synthesizing natural base steroidal hormones (phytoestrogens and phytoprogesterone) of the present invention have been developed to provide a "natural" means for enhancing, supplementing and/or maintaining the hormonal balance of living organisms while foregoing the undesirable physiological side effects. Correspondingly, natural base steroidal hormones synthesized and/or extracted by the systems and methods of the present invention are presumed to be distributed, metabolized, and excreted in the same manner as endogenous estrogens and progesterone synthesized and metabolized within biological organisms.

The term "steroidal hormone" as used hereinafter in the specification and the claims includes all natural based estrogens and progesterone and estrogen-like and progesterone-like compounds which demonstrate substantially the same physiological effects as steroidal hormones having the chemical formulas $C_{18}H_{24}O_2$ and $C_{21}H_{30}O_2$. Similarly, the natural base steroidal hormones which are to be treated in accordance with the present invention may be considered as having the following structural formulas:

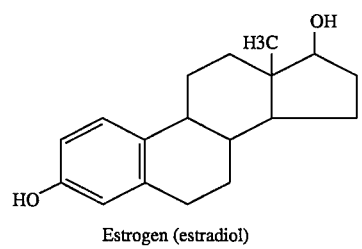

Estrogen (estradiol)

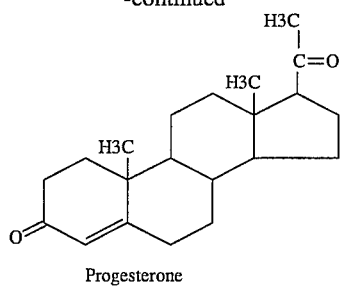

Progesterone

The above structural formulas are merely illustrative and are not intended to limit the present invention which includes other compounds and derivatives of similar constitution although differing in the number and position of hydrogen and/or oxygen atoms.

The following compositions and formulations, suitable for human consumption (by oral ingestion or extract), parenteral injection or topical application have been formulated and are representative of the invention. The following examples, however, serve only to illustrate the invention and are not intended to be limiting of the same:

EXAMPLE I

Natural base steroidal hormones derived as phytohormones (phytoestrogens and/or phytoprogesterone) from herbaceous plants was formulated from an herbal mixture of black cohosh (1135 grams), sarsaparilla (681 grams), licorice (681 grams), false unicorn (454 grams), dong quai (454 grams), wild yam root (454 grams), squaw vine (454 grams), and damiana (454 grams). The powdered ingredients in the quantities defined are mixed to produce a single batch and then encapsulated into gelatin capsules. Each capsule was formulated to contain approximately 575 mgs. of the foregoing natural compounds.

EXAMPLE II

Natural base steroidal hormones derived as phytohormones (phytoestrogens and/or phytoprogesterone) from herbaceous plants was formulated from an herbal mixture of black cohosh (1135 grams), sarsaparilla (681 grams), licorice (681 grams), false unicorn (454 grams), dong quai (454 grams), blessed thistle (28 grams), squaw vine (454 grams) and damiana (454 grams). The powdered ingredients in the quantities defined are mixed to produce a single batch and then encapsulated into gelatin capsules. Each capsule was formulated to contain approximately 575 mgs. of the foregoing natural compounds in a powdered form.

EXAMPLE III

Natural base steroidal hormones derived as phytohormones (phytoestrogens and/or phytoprogesterone) from herbaceous plants was formulated from an herbal mixture of black cohosh (1135 grams), sarsaparilla (681 grams), licorice (681 grams), false unicorn (454 grams), dong quai (454 grams), wild yam root (454 grams), squaw vine (454 grams), damiana (454 grams), raspberry (454 grams), burdock (454 grams) and peony (454 grams). The powdered ingredients in the quantities defined are mixed to produce a single batch and then encapsulated into gelatin capsules. Each capsule was formulated to contain approximately 575 mgs. of the foregoing natural compounds.

EXAMPLE IV

Natural base steroidal hormones derived as phytohormones (phytoestrogens and/or phytoprogesterone) from herbaceous plants was formulated from an herbal mixture of black cohosh (1135 grams), sarsaparilla (681 grams), licorice (681 grams), false unicorn (454 grams), dong quai (454 grams), blessed thistle (28 grams), squaw vine (454 grams), damiana (454 grams), raspberry (454 grams), burdock (454 grams) and peony (454 grams). The powdered ingredients in the quantities defined are mixed to produce a single batch and then encapsulated into gelatin capsules. Each capsule was formulated to contain approximately 575 mgs. of the foregoing natural compounds in a powdered form.

EXAMPLE V

Natural base steroidal hormones derived as phytohormones (phytoestrogens and/or phytoprogesterone) from herbaceous plants was formulated from an herbal mixture of black cohosh, sarsaparilla, licorice, dong quai, wild yam root, and damiana. The powdered ingredients are mixed to produce a single batch and then encapsulated into gelatin capsules. Each capsule was formulated to contain approximately 575 mgs. of the foregoing natural compounds in a powdered form.

EXAMPLE VI

Natural base steroidal hormones derived as phytohormones (phytoestrogens and/or phytoprogesterone) from herbaceous plants was formulated from an herbal mixture of black cohosh, licorice, false unicorn, dong quai, wild yam root, squaw vine, and damiana. The powdered ingredients are mixed to produce a single batch and then encapsulated into gelatin capsules. Each capsule was formulated to contain approximately 575 mgs. of the foregoing natural compounds in a powdered form.

EXAMPLE VII

Natural base steroidal hormones derived as phytohormones (phytoestrogens and/or phytoprogesterone) from herbaceous plants was formulated from an herbal mixture of black cohosh, licorice, false unicorn, dong quai, wild yam root, and damiana. The powdered ingredients are mixed to produce a single batch and then encapsulated into gelatin capsules. Each capsule was formulated to contain 575 mgs. of the foregoing natural compounds in a powdered form.

EXAMPLE VIII

Natural base steroidal hormones derived as phytohormones (phytoestrogens and/or phytoprogesterone) from herbaceous plants was formulated from an herbal mixture of black cohosh, sarsaparilla, false unicorn, dong quai, wild yam root, squaw vine, and damiana. The powdered ingredients are mixed to produce a single batch and then encapsulated into gelatin capsules. Each capsule was formulated to contain 575 mgs. of the foregoing natural compounds in a powdered form.

EXAMPLE IX

Natural base steroidal hormones derived as phytohormones (phytoestrogens and/or phytoprogesterone) from herbaceous plants was formulated from an herbal mixture of black cohosh, sarsaparilla, licorice, false unicorn, dong quai, wild yam root, squaw vine, damiana and raspberry. The powdered ingredients in the quantities defined are mixed to produce a single batch and then encapsulated into gelatin capsules. Each capsule was formulated to contain approximately 575 mgs. of the foregoing natural compounds.

EXAMPLE X

Natural base steroidal hormones derived as phytohormones (phytoestrogens and/or phytoprogesterone) from herbaceous plants was formulated from an herbal mixture of black cohosh, sarsaparilla, licorice, false unicorn, dong quai, wild yam root, squaw vine, damiana and burdock. The powdered ingredients in the quantities defined are mixed to produce a single batch and then encapsulated into gelatin capsules. Each capsule was formulated to contain approximately 575 mgs. of the foregoing natural compounds.

EXAMPLE XI

Natural base steroidal hormones derived as phytohormones (phytoestrogens and/or phytoprogesterone) from herbaceous plants was formulated from an herbal mixture of black cohosh, sarsaparilla, licorice, false unicorn, dong quai, wild yam root, squaw vine, damiana and peony. The powdered ingredients in the quantities defined are mixed to produce a single batch and then encapsulated into gelatin capsules. Each capsule was formulated to contain approximately 575 mgs. of the foregoing natural compounds.

EXAMPLE XII

Natural base steroidal hormones derived as phytohormones (phytoestrogens and/or phytoprogesterone) from herbaceous plants was formulated from an herbal mixture of black cohosh, sarsaparilla, licorice, false unicorn, dong quai, blessed thistle, squaw vine, damiana, raspberry, burdock and peony. The powdered ingredients in the quantities defined are mixed to produce a single batch and then encapsulated into gelatin capsules. Each capsule was formulated to contain approximately 575 mgs. of the foregoing natural compounds in a powdered form.

EXAMPLE XIII

An alternate preferred formulation of the systems and methods for synthesizing natural base steroidal hormones, the present invention is synthesized as an emulsified cream, gel or ointment for topical application to the soft skin areas of the body. Preferably, approximately six percent (6%) wild yam extract is mixed with one or more herbaceous compounds having phytohormone (phytoestrogen and/or phytoprogesterone) characteristics selected from the group consisting of black cohosh, sarsaparilla, licorice, false unicorn, dong quai, squaw vine, damiana, raspberry, burdock, peony and ginseng, in accordance with one preferred method as outlined in the following steps. Various phytoliposomes may also be added to the formulation to assist in the transportation of nutrients through the skin for absorption into the circulatory system of the biological organism.

Beginning with an oil phase, approximately 15% grapeseed oil is introduced into a mixing vessel wherein approximately 1.5% lecithin is slowly added to the grapeseed oil and mixed for approximately two (2) minutes or until totally dispersed. The grapeseed oil/lecithin mixture is heated to approximately 80° C. and set aside to cool to approximately 60° C.

Next, a water phase is prepared by mixing approximately 6% distilled water with approximately 2% vegetable glycerin, approximately 0.25% methylparaben, and approximately 0.25% propylparaben for approximately sixty (60) seconds. The mixture produced from the water phase is then heated to approximately 70° C. and set aside to cool to approximately 60° C.

Approximately 18% distilled water is introduced into a mixing vessel wherein approximately 15% cellulose gel (i.e., Natrosol™) is slowly added to the distilled water and mixed for approximately sixty (60) seconds. The distilled water/cellulose gel mixture is then set aside to form a gelatinous medium which takes approximately ten (10) minutes before the gel begins to set.

A mixture of actives consisting of approximately 30% aloe vera juice, approximately 6% wild yam extract, approximately 5% of one or more herbaceous compounds having phytohormone (phytoestrogen and/or phytoprogesterone) characteristics selected from the group consisting of black cohosh, sarsaparilla, licorice, false unicorn, dong quai, wild yam, squaw vine, damiana, raspberry, burdock and peony (or any of the combinations disclosed in Examples I through VI above), approximately 0.25% licorice phytosomes, and approximately 0.25% ginseng phytosomes are mixed for approximately sixty (60) seconds.

After both the oil phase mixture and the water phase mixture have cooled to approximately 60° C., the oil phase mixture and the water phase mixture are mixed together for approximately two (2) minutes. The oil phase/water phase mixture is then slowly mixed (which can be done by hand) with the above-identified mixture of actives. The oil phase/water phase mixture in combination with the active mixture is then slowly mixed with the gelatinous medium to formulate an emulsified gel, cream or ointment promoting hormone replacement or balancing activity when used as a topical application to the skin by means of, for example, a convenient roll-on applicator head. Moreover, the pH of the emulsified gel, cream or ointment is preferably tested and adjusted by adding sodium bicarbonate in order to establish an emulsified gel, cream or ointment having a 6.5 pH.

From the above discussion, it will be appreciated that the present invention provides means of delivering natural base steroidal hormones such as estrogens and progesterone and estrogen-like and progesterone-like compounds and their derivatives derived as phytohormones from herbaceous plants to specific target sites within a living organism for enhancing, supplementing, and/or maintaining estrogenic and/or progesterone hormone levels in order to assist hormonal-dependent body functions and physiological processes within biological organisms. Unlike prior art chemical base steroidal hormones, the present invention provides means for balancing estrogen and progesterone hormonal levels in biological organisms without encouraging undesirable physiological side effects and therapeutic contraindications.

Additionally, the present invention provides systems and methods for synthesizing natural base steroidal hormones such as estrogens and progesterone and estrogen-like and progesterone-like compounds and their derivatives derived as phytohormones (phytoestrogen and/or phytoprogesterone) from herbaceous plants and which are sufficiently stable when properly formulated, in that they are readily absorbed into biological systems and transported to target sites for utilization. Moreover, the present invention is formulated as a natural dietary food supplement which can be produced at a very minimal cost.

The present invention may be embodied in other specific embodiments, formulations or compilations without departing from its spirit or essential characteristics. The invention, of course, is not limited to the examples described above, but various changes may be made in the details disclosed in the foregoing specification in accordance with the principles set forth herein and in the claims annexed hereto. All changes which come within the meaning and range of equivalency of the claims are to be embraced within their scope.

What is claimed and desired to be secured by United States Letters Patent is:

1. A process for preparing an active mixture of natural base steroidal hormones for supplementing estrogen and progesterone levels of a biological organism, comprising:

mixing approximately 454 grams of wild yam, approximately 681 grams of sarsaparilla, approximately 681 grams of licorice, approximately 1135 grams of black cohosh, approximately 454 grams of damiana, and approximately 454 grams of dong quai, to obtain a uniform dispersion of said active mixture in a powdered form; and encapsulating approximately 575 milligrams of said active mixture into a gelatin capsule.

2. A process for preparing an active mixture of natural base steroidal hormones for supplementing estrogen and progesterone levels of a biological organism, comprising:

mixing approximately 454 grams of wild yam, approximately 681 grams of sarsaparilla, approximately 681 grams of licorice, approximately 1135 grams of black cohosh, approximately 454 dong quai, approximately 454 grams of false unicorn, approximately 454 grams of squaw vine, approximately 454 grams of damiana, approximately 454 grams of raspberry, approximately 454 grams of peony, and approximately 454 grams of burdock, to obtain a uniform dispersion of said active mixture in a powdered form; and encapsulating approximately 575 milligrams of said active mixture into a gelatin capsule.

3. A process for preparing an active mixture of natural base steroidal hormones as defined in claim 2 further comprising replacing said wild yam with approximately 28 grams of blessed thistle.

4. A process for preparing a gel comprising natural base steroidal hormones for supplementing estrogen and progesterone levels of a biological organism, comprising:

mixing approximately 454 grams of wild yam, approximately 681 grams of sarsaparilla, approximately 681 grams of licorice, approximately 1135 grams of black cohosh, approximately 454 grams of damiana, and approximately 454 grams of dong quai, to obtain a uniform dispersion of an active mixture in a powdered form;

mixing grapeseed oil with a digestible emulsifier until dispersed to obtain a first mixture and heating said first mixture to approximately 80° C. and then cooling said first mixture to approximately 60° C.;

mixing distilled water with a vegetable glycerin until dispersed to obtain a second mixture and heating said second mixture to approximately 70° C. and then cooling said second mixture to approximately 60° C.;

preparing a gelatinous medium by mixing a cellulose gel with distilled water and allowing said medium to gelatinize;

mixing the first mixture with the second mixture to provide a third mixture;

mixing said active mixture with said third mixture to provide a fourth mixture;

mixing said fourth mixture with said gelatinous medium to form said emulsified gel; and adjusting a pH of said emulsified gel to accommodate approximately a 6.5 pH balance.

5. A process for preparing a gel comprising natural base steroidal hormones as defined in claim 4 further comprising introducing approximately 454 grams of false unicorn and approximately 454 grams of squaw vine to said active mixture.

6. A process for preparing a gel comprising natural base steroidal hormones as defined in claim 4 further comprises introducing aloe vera juice, licorice phytosomes, and ginseng phytosomes.

7. A process for preparing a gel comprising natural base steroidal hormones as defined in claim 4 wherein adjusting said pH comprises adding an alkaline pH-modifying substance.

8. A process for preparing a gel comprising natural base steroidal hormones as defined in claim 4 further comprising replacing said wild yam with approximately 28 grams of blessed thistle.

9. A process for preparing a gel comprising natural base steroidal hormones as defined in claim 4 further comprising introducing approximately 0.25% of methylparaben and approximately 0.25% of propylparaben into said second mixture.

10. A process for preparing an emulsified gel comprising natural base steroidal hormones for supplementing estrogen and progesterone levels of a biological organism, comprising:

mixing approximately 15% grapeseed oil with approximately 1.5% of a digestible emulsifier until dispersed to obtain a first mixture and heating said first mixture to approximately 80° C. and then cooling said first mixture to approximately 60° C.;

mixing approximately 6.06% distilled water and approximately 2% vegetable glycerin until dispersed to obtain a second mixture and heating said second mixture to approximately 70° C. and then cooling said second mixture to approximately 60° C.;

preparing a gelatinous medium by mixing approximately 15% cellulose gel with approximately 18.19% distilled water until dispersed and allowing said medium to gelatinize;

mixing approximately 681 grams of sarsaparilla, approximately 681 grams of licorice, approximately 1135 grams of black cohosh, approximately 454 grams of damiana, approximately 454 grams of dong quai and approximately 454 grams of burdock, to obtain a uniform dispersion of an active mixture in a powdered form;

mixing said first mixture and said second mixture to form a third mixture;

mixing said third mixture with approximately 5% of said active mixture and introducing approximately 6% wild yam, approximately 30% aloe vera juice, approximately 0.25% licorice phytosomes, and approximately 0.50% ginseng phytosomes to form a fourth mixture;

mixing said fourth mixture with said gelatinous medium to form said emulsified gel;

testing a pH of said emulsified gel;

adjusting said pH of said emulsified gel by adding an alkaline pH-modifying substance to accommodate approximately a 6.5 pH balance.

11. A process for preparing an emulsified gel comprising natural base steroidal hormones as defined in claim 10 further comprising introducing approximately 0.25% of methylparaben and approximately 0.25% of propylparaben into said second mixture.

12. A process for preparing an emulsified gel comprising natural base steroidal hormones as defined in claim 10 further comprising introducing approximately 454 grams of false unicorn, approximately 454 grams of squaw vine, approximately 454 grams of damiana, and approximately 454 grams of peony into said active mixture.

13. A process for preparing an emulsified gel comprising natural base steroidal hormones as defined in claim 10 wherein said alkaline pH-modifying substance comprises introducing a sufficient quantity of sodium bicarbonate to accommodate said 6.5 pH balance.

14. A process for preparing an emulsified gel comprising natural base steroidal hormones as defined in claim 10 wherein said digestible emulsifier comprises lecithin.

15. A process for preparing an active mixture of natural base steroidal hormones as defined in claim 1 further comprising introducing approximately 454 grams of false unicorn into said active mixture.

16. A process for preparing an active mixture of natural base steroidal hormones as defined in claim 1 further comprising introducing approximately 454 grams of squaw vine into said active mixture.

17. A process for preparing an active mixture of natural base steroidal hormones as defined in claim 1 further comprising replacing said wild yam with approximately 28 grams of blessed thistle.

18. A process for preparing an active mixture of natural base steroidal hormones for supplementing estrogen and progesterone levels of a biological organism, comprising:

mixing approximately 1135 grams of black cohosh, approximately 681 grams of sarsaparilla, approximately 681 grams of licorice, approximately 454 grams of false unicorn, approximately 454 grams of dong quai, approximately 454 grams of wild yam, approximately 454 grams of squaw vine, and approximately 454 grams of damiana, to obtain a uniform dispersion of said active mixture in a powdered form; and encapsulating approximately 575 milligrams of said active mixture into a gelatin capsule.

19. A process for preparing an active mixture of natural base steroidal hormones as defined in claim 18 further comprising replacing said wild yam with approximately 28 grams of blessed thistle.

* * * * *